United States Patent [19]

Gruber et al.

[11] 4,233,441
[45] Nov. 11, 1980

[54] COPOLYMERIZABLE, ULTRAVIOLET LIGHT ABSORBER 4-ACRYLOXYBENZAL-3-ALKYL-2 N-BENZOTHIAZOLOAZINES

[75] Inventors: Bruce A. Gruber, Worthington, Ohio; Donald H. Lorenz, Basking Ridge, N.J.

[73] Assignee: GAF Corporation, New York, N.Y.

[21] Appl. No.: 90,046

[22] Filed: Oct. 31, 1979

[51] Int. Cl.³ .................................. C07D 277/82
[52] U.S. Cl. .......................... 542/419; 260/45.8 SN; 548/161
[58] Field of Search ............... 542/419; 260/45.8 SN; 548/161

[56] References Cited
U.S. PATENT DOCUMENTS

| | | | |
|---|---|---|---|
| 2,659,730 | 11/1953 | Katz | 542/419 |
| 3,417,082 | 12/1968 | Taylor | 542/419 |
| 4,105,631 | 8/1978 | Wange et al. | 260/45.8 SN |

OTHER PUBLICATIONS

Kirk–Othmer, Encyclopedia of Polymer Science and Technology, vol. 12, 1970, pp. 725–726.

*Primary Examiner*—Arthur P. Demers
*Attorney, Agent, or Firm*—Walter C. Kehm; Walter Katz

[57] ABSTRACT

This invention relates to copolymerizable ultraviolet light absorber compounds having the formula:

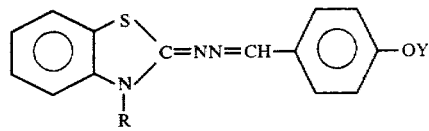

where
R is alkyl $C_1$–$C_6$; and
Y is a copolymerizable radical selected from acryloyl $C_3$–$C_{12}$, acryloxyalkyl $C_3$–$C_{12}$, acryloxyhydroxyalkyl $C_3$–$C_{12}$, and alkylacryloxyhydroxyalkyl $C_3$–$C_{12}$.

7 Claims, No Drawings

COPOLYMERIZABLE, ULTRAVIOLET LIGHT ABSORBER 4-ACRYLOXYBENZAL-3-ALKYL-2 N-BENZOTHIAZOLOAZINES

BACKGROUND OF THE INVENTION

1. Field of the Invention

This invention relates to novel copolymerizable ultraviolet light absorber compounds, and, more particularly, to 4-acryloxybenzal-3'-alkyl-2'-N-benzothiazoloazine compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultra-violet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultra-violet absorbers with radiation curing of the plastic material. Another disadvantage of these ultra-violet absorbers is the high amount of absorber needed for protection of some materials.

Still another limitation on the use of prior art absorbers is that they provide little or no protection in the 330 to 400 nm region, which is a desirable region when the absorbers are used for skin and hair care products, such as suntan preparations and hair dye and hair tinting compositions.

Accordingly, it is an object of the present invention to provide novel copolymerizable ultraviolet light absorber compounds which are substantially free of the disadvantages of the prior art.

A particular object of this invention is to provide novel compounds which can be copolymerized directly with monomers, such as plastic material, to provide more permanent ultraviolet light protection.

A specific object is to provide ultraviolet light absorber compounds containing a copolymerizable acryloyl group which exhibits absorption in the 330 to 400 nm region.

These and other objects and features of the invention will be made apparent from the following more particular description of the invention.

SUMMARY OF THE INVENTION

What is provided herein are improved, novel copolymerizable ultraviolet light absorber compounds of the formula:

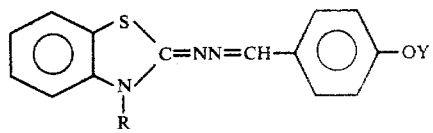

where
R is alkyl $C_1$–$C_6$; and
Y is a copolymerizable radical selected from acryloyl $C_3$–$C_{12}$, alkylacryloyl $C_3$–$C_{12}$, acryloxyalkyl $C_3$–$C_{12}$, and alkylacryloxyhydroxyalkyl $C_3$–$C_{12}$.

In the best mode of the invention, R is methyl and Y is acryloyl.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the absorber portion does not inhibit the copolymerization, and the ethylenic radical does not affect the light absorbing properties of the molecule.

The Y radical is copolymerizable with vinyl monomers so that the ultraviolet absorber becomes an integral part of the polymer. Suitable Y groups are derived from acryloyl, alkylacryloyl, acryloxyalkyl, acryloxyhydroxyalkyl and alkylacryloxyhydroxyalkyl, having from $C_3$–$C_{12}$ carbon atoms. The preferred groups are acryloyl, methacryloyl, acryloxyhydroxypropyl, and methacryloxyhydroxypropyl. The best mode is represented by acryloyl.

The novel compounds of the invention may be prepared from 4-hydroxybenzal-3'-alkyl-2'-N-benzothiazoloazine by esterification with an acryloyl halide.

The starting material for the esterification is obtained by condensing the commercially available (Aldrich Chem. Co.) 3-alkyl-2-benzothiazolone hydrazone hydrochloride monohydrate with p-hydroxybenzaldehyde.

The novel compound of the inventions are colorless solids which are insoluble in water. The benzal benzothiazoloazine chromophore of the compounds herein has an ultraviolet absorbence peak at about 350 nm, but no visible absorbance.

The 3-alkyl-2-benzothiazolone hydrazone may be prepared from the corresponding 3-alkyl-2-methylthiobenzothiazolium p-toluene sulfonate by reaction with formylhydrazine in aqueous solution at reflux temperatures. The desired intermediate is obtained upon basification of the solution, giving a precipitate of the compound in yields of 60–70%.

The flow sheet below illustrates the reaction sequence for preparing the compounds of the invention.

Step (a)

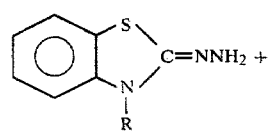

-continued

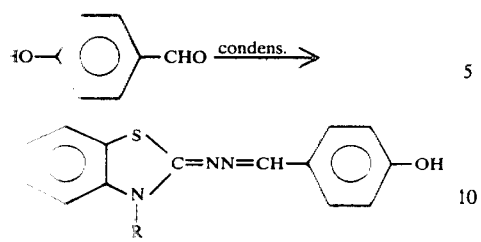

Step (b)

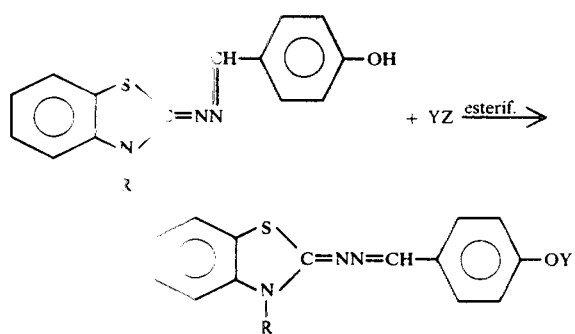

where Z is a halide and R and Y are as defined above.
Representative Y groups are

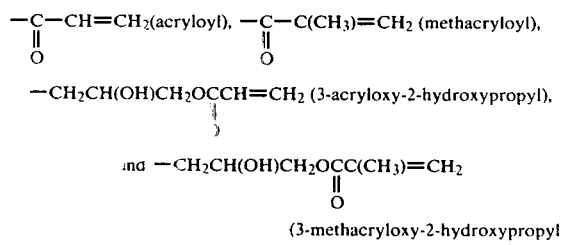

In step (a), the hydrazone is dispersed in ethanol with sodium acetate. Then p-hydroxybenzaldehyde and acetic acid in ethanol are added with stirring until the azine separates. The product is filtered and the yield is nearly quantitative.

The esterification step (b) is carried out with a reactive acryloyl compound, such as an acryloyl halide, e.g. acryloyl chloride or acryloyl bromide, in aqueous base, such as a sodium hydroxide solution, at room temperature. Suitably the molar ratios of the reactants are controlled to provide at least 1:1 molar ratio of the acryloyl halide to the hydroxy intermediate. The product of the reaction precipitates, is filtered, and dried. The yield of the product in step (b) is about 80–90%.

The compounds of the invention may be copolymerized with monomers and oligomers by conventional free radical or with radiation curing, to provide useful polymeric coatings, or formulated into cosmetic preparations, such as skin and hair care products.

The following examples will describe the invention with more particularity.

EXAMPLE 1

4-Acryloxybenzal-3'-Methyl-2'-N-Benzothiazoloazine

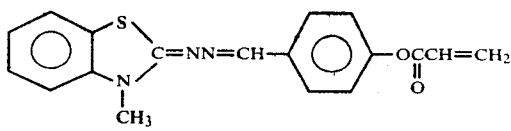

Step (a)

4-Hydroxybenzal-3'-Methyl-2'-N-Benzothiazloazine

Into a flask equipped with a mechanical stirrer is charged 17.9 g (0.1 mole) of 3-methyl-2-benzothiazolone hydrazone monohydrate, 500 ml absolute ethanol and 12 g sodium acetate. To the rapidly stirred suspension then is added 20 ml absolute ethanol containing 12 g (0.1 mole) p-hydroxybenzaldehyde and 5 ml glacial acetic acid. The suspension is stirred for 1 hour, then filtered, giving 28 g (98%) of a light tan solid; mp 252°–254° C., nmr (DMSO-$d_6$) δ 3.5 (S, 3H), 7.3 (m, 8H), 8.3 (S, 1H), 9.8 (S, 1H).

Step (b)

To a solution of 1.95 g. (0.049 moles) of sodium hydroxide in 150 ml water is added 13.8 g (0.049 moles) of 4-hydroxybenzal-3'-methyl-2'-N-benzothiazoloazine. After dissolving completely, 4.41 g (0.049 moles) of acryloyl chloride is added dropwise to the solution. A white precipitate separates which is filtered and dried to provide an off-white powder, weighing 14.2 g (86%); nmr (DMSO-$d_6$) δ 3.5 (d, 3H), 6.2 (m, 3H), 7.2 (m, 8H), 8.2 (d, 1H).

EXAMPLE 2

4-Methacryloyloxybenzal-3'-Methyl-2'-N-Benzothiazoloazine

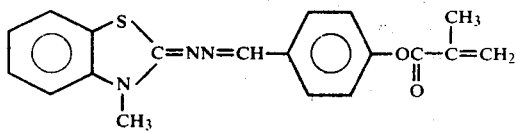

Using an equivalent amount of methacryloyl chloride in place of acryloyl chloride in Step (b) of Example 1, the desired methacrylate compound is obtained in comparable yield.

EXAMPLE 3

4-(3-Acryloxy-2-Hydroxypropyl)oxybenzal-3'-Methyl-2'-N-Benzothiazoloazine

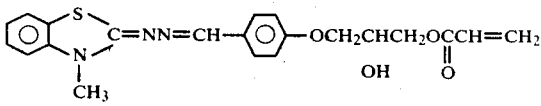

The procedure of Example 1 is followed except that (a), glycidyl acrylate and tetramethylammonium chloride are heated at 70°–90° C. for 5 hrs., and excess glycidal acrylate removed by vac distillation, to provide the desired compound.

EXAMPLE 4

4-(3-Methacryloxy-2-Hydroxypropyl)oxybenzal-3'-Methyl-2'-N-Benzothiazoloazine

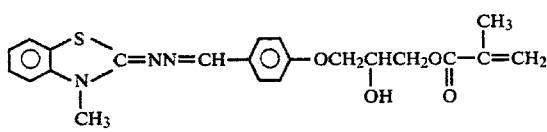

Using glycidyl methacrylate in place of glycidyl acrylate in Example 3 gives the corresponding methacrylate compound.

EXAMPLE 5

3-Methyl-2-Benzothiazolone Hydrazone

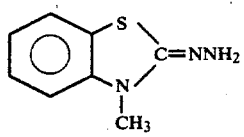

Into a flask equipped with a reflux condenser and magnetic stirrer is charged 50 ml water. Then 28.1 g (0.076 moles) 3-methyl-2-methylthiobenzothiazoium p-toluene sulfonate is dissolved with slight heating. A solution of 9.1 g (0.15 moles) formylhydrazine in 25 ml of water then is added and the mixture is heated at reflux for 15 minutes. The cooled suspension is made acidic until a clear solution results, then made basic. The product precipitates and is filtered, giving 9.1 g (66%), m.p. 134° C.

EXAMPLE 6

The monomer compound of Example 1 is copolymerized with another monomer by charging a flask with 150 ml ethanol, 1.5 g 4-acryloxybenzal-3'-methyl-2'-benzothiazoloazine and 50 g vinyl pyrrolidone. The contents are heated to 75° C. under $N_2$ and polymerization is initiated with 0.2 g azobis-isobutyronitrile (AIBN). After 1.5 hrs., another 0.2 g AIBN is added and heating is continued for another 1.5 hrs. The solvent is concentrated and added to stirred ether. A white precipitate of the copolymer is obtained which is filtered and dried, giving 18 g (36%) of product. A 5% aqueous solution of the copolymer is filtered; the ultraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. Copolymerizable ultraviolet light absorber compounds having the formula:

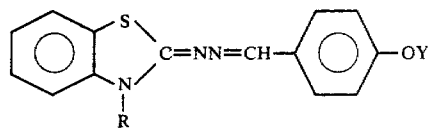

where

R is alkyl $C_1$–$C_6$; and

Y is a copolymerizable radical selected from acryloyl $C_3$–$C_{12}$, alkylacryoyl $C_3$–$C_{12}$, acryloxyalkyl $C_3$–$C_{12}$, acryloxyhydroxyalkyl $C_3$–$C_{12}$, and alkylacryloxyhydroxyalkyl $C_3$–$C_{12}$.

2. Compounds according to claim 1 wherein R is methyl.

3. Compounds according to claim 1 in which Y is acryloyl, methacryloyl, 3-acryloxy-2-hydroxypropyl or 3-methacryloxy-2-hydroxypropyl.

4. A compound according to claim 1 which is 4-acryloxybenzal-3'-methyl-2'-benzothiazoloazine.

5. A compound according to claim 1 which is 4-methacryloxybenzal-3'-methyl-2'-N-benzothizoloazine.

6. A compound according to claim 1 which is 4-(3-acryloxy-2-hydroxypropyl)oxybenzal-3'-methyl-2'-N-benzothiazoloazine.

7. A compound according to claim 1 which is 4-(3-methacryloxy-2-hydroxypropyl)oxybenzal-3'-methyl-2'-N-benzothiazoloazine.

* * * * *